(12) United States Patent
Nishida et al.

(10) Patent No.: US 9,255,939 B2
(45) Date of Patent: Feb. 9, 2016

(54) SAMPLE ANALYZER AND A COMPUTER PROGRAM PRODUCT

(75) Inventors: Tomoyuki Nishida, Ashiya (JP); Takatomo Kudo, Kobe (JP); Hiroto Toyoshima, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 502 days.

(21) Appl. No.: 12/288,562

(22) Filed: Oct. 21, 2008

(65) Prior Publication Data

US 2009/0226344 A1 Sep. 10, 2009

(30) Foreign Application Priority Data

Mar. 4, 2008 (JP) ................................. 2008-052954

(51) Int. Cl.
*G01N 35/10* (2006.01)
*G01N 35/04* (2006.01)

(52) U.S. Cl.
CPC .... *G01N 35/1011* (2013.01); *G01N 2035/0491* (2013.01); *G01N 2035/0494* (2013.01); *G01N 2035/1013* (2013.01)

(58) Field of Classification Search
CPC ................... G01N 35/011; G01N 2035/1013; G01N 2035/0491; G01N 2035/0494
See application file for complete search history.

(56) References Cited

U.S. PATENT DOCUMENTS

| 5,443,790 | A | * | 8/1995 | Coeurveille et al. | ............. 422/63 |
| 5,443,792 | A | * | 8/1995 | Buhler | .............. 422/67 |
| 6,270,726 | B1 | * | 8/2001 | Tyberg et al. | .................. 422/509 |
| 2005/0178795 | A1 | * | 8/2005 | Inoue | ............... 222/23 |
| 2006/0081539 | A1 | * | 4/2006 | Safar et al. | ..................... 210/695 |
| 2007/0065945 | A1 | * | 3/2007 | Sigrist | .............................. 436/43 |
| 2007/0148042 | A1 | | 6/2007 | Ootani et al. | |
| 2008/0101990 | A1 | * | 5/2008 | Liu et al. | .......................... 422/63 |

FOREIGN PATENT DOCUMENTS

| JP | 3-183958 | * | 8/1991 |
| JP | 11-160326 | * | 6/1999 |
| JP | 2001-091522 | | 4/2001 |

* cited by examiner

*Primary Examiner* — P. Kathryn Wright
(74) *Attorney, Agent, or Firm* — Brinks Gilson & Lione

(57) ABSTRACT

A sample analyzer comprises a pipette, a pipette moving mechanism and a position confirming member disposed at a position where the pipette can be moved by the pipette moving mechanism. The position confirming member comprises a space into which a tip end of the pipette can be inserted. When the sample analyzer carries out the position confirmation process, the tip end of the pipette is moved by the pipette moving mechanism so as to be inserted into the space of the position confirming member. When a sensor sensed that the tip end of the pipette collides with the position confirming member, the sample analyzer stops the movement of the pipette and notify that the pipette of the pipette moving mechanism has a problem.

12 Claims, 9 Drawing Sheets

SAMPLE ANALYZER AND A COMPUTER PROGRAM PRODUCT

RELATED APPLICATIONS

This application claims priority under 35 U.S.C. §119 to Japanese Patent Application No. JP2008-052954 filed on Mar. 4, 2008, the entire content of which is hereby incorporated by reference.

FIELD OF THE INVENTION

The present invention relates to a sample analyzer for analyzing a sample, such as an immunological analyzer and a blood-clotting analyzer. In addition, the invention relates to a computer program product for use in the sample analyzer.

BACKGROUND

There has been known a sample analyzer for analyzing components of a sample by subjecting a specimen prepared by mixing the sample and a reagent to a measuring operation. The sample analyzer has a reagent dispensing section configured to suction the reagent from a reagent container containing the reagent and to eject the suctioned reagent into a cuvette (reaction container). The operation of the reagent dispensing section is controlled by a control section provided in the sample analyzer in accordance with a predetermined operation sequence.

The reagent container is provided with an opening to which a pipette of the reagent dispensing section is inserted to suction the reagent. In order to prevent the reagent from being vaporized or contaminated, the opening is formed as small as possible. For this reason, the reagent cannot be properly suctioned when the pipette is not accurately positioned in the opening.

Accordingly, in order to properly dispense the reagent, it is necessary to adjust the pipette so as to be accurately positioned at a predetermined position.

JP2001-91522 discloses that a pipette of a dispensing section is adjusted so as to be positioned at a predetermined position. According to JP2001-91522, the adjustment of the pipette of the dispensing section is performed in such a manner that a user executes a predetermined adjustment program when mounting an analyzer or exchanging a dispensing section-related part.

When the sample analyzer is used for a long period of time, deterioration of a mechanism for driving the reagent dispensing section (extending of a driving belt, and the like), and the like may cause gradual displacement of a stop position of the pipette. Further, the pipette may be bent when the user touches the pipette of the dispensing section. In this case, when the analyzer performs an analyzing operation, it is difficult to accurately position a tip end of the pipette at a predetermined position and thus the pipette may be brought into contact with a reagent container and be thereby damaged.

In a technique of JP2001-91522, the pipette can be adjusted so as to be positioned at a predetermined position. However, the pipette damage caused by prolonged use of the sample analyzer cannot be prevented.

SUMMARY OF THE INVENTION

A first aspect of the invention is a sample analyzer comprising: a pipette for dispensing a reagent or a sample; a pipette moving mechanism for moving the pipette; a position confirming section disposed at a position where the pipette can be reached; and a controller for performing a position confirming process comprising: moving the pipette by the pipette moving mechanism so as to be disposed at a predetermined position included in the position confirming section; and judging whether the moved pipette is disposed at the predetermined position.

A second aspect of the invention is a sample analyzer comprising: a pipette for dispensing a reagent or a sample; a pipette moving mechanism for moving the pipette; a position confirming section disposed at a position where the pipette can be reached; and a controller, including a memory under control of a processor, the memory storing instructions enabling the processor to carry out operations, comprising: moving the pipette by the pipette moving mechanism so as to be disposed at a predetermined position included in the position confirming section; and judging whether the pipette moved by the moving step is disposed at the predetermined position.

A third aspect of the invention is a computer program product comprising: a computer readable medium; and instructions, on the computer readable medium, adapted to enable a sample analyzer, comprising a pipette for dispensing a reagent or a sample, a pipette moving mechanism for moving the pipette, and a position confirming section disposed at a position where the pipette can be reached, to perform operations, comprising: moving the pipette by the pipette moving mechanism so as to be disposed at a predetermined position included in the position confirming section; and judging whether the pipette moved by the moving step is disposed at the predetermined position.

DETAILED DESCRIPTION OF THE PREFERRED EMBODIMENTS

Hereinafter, embodiments of a sample analyzer of the invention will be described in detail with reference to the accompanying drawings.

[Overall Configuration of Device]

Figure 1:
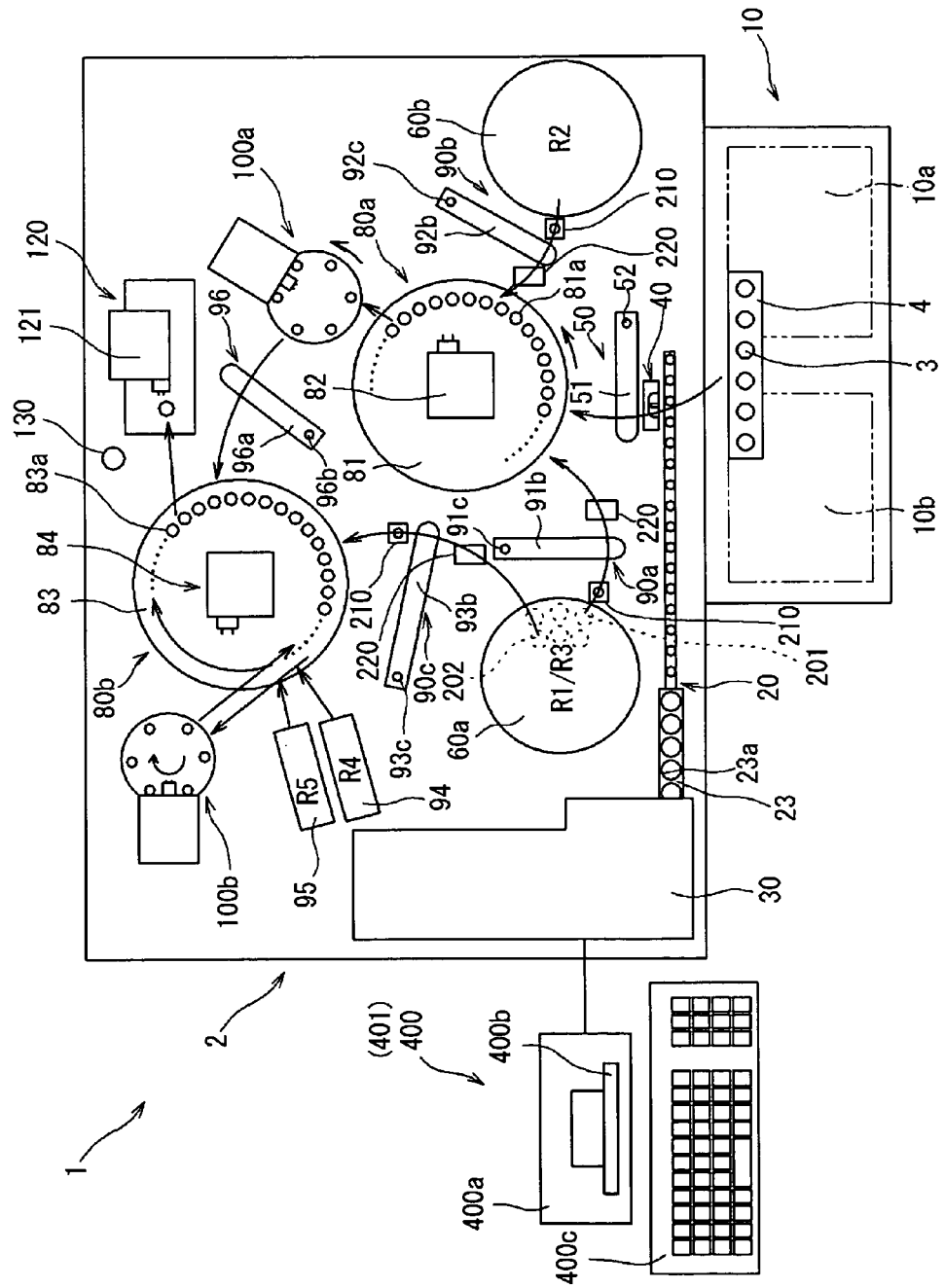
FIG. 1 is a plan explanatory diagram illustrating the overall configuration of an immunological analyzer (sample analyzer) according to an embodiment of the invention.
Figure 2:
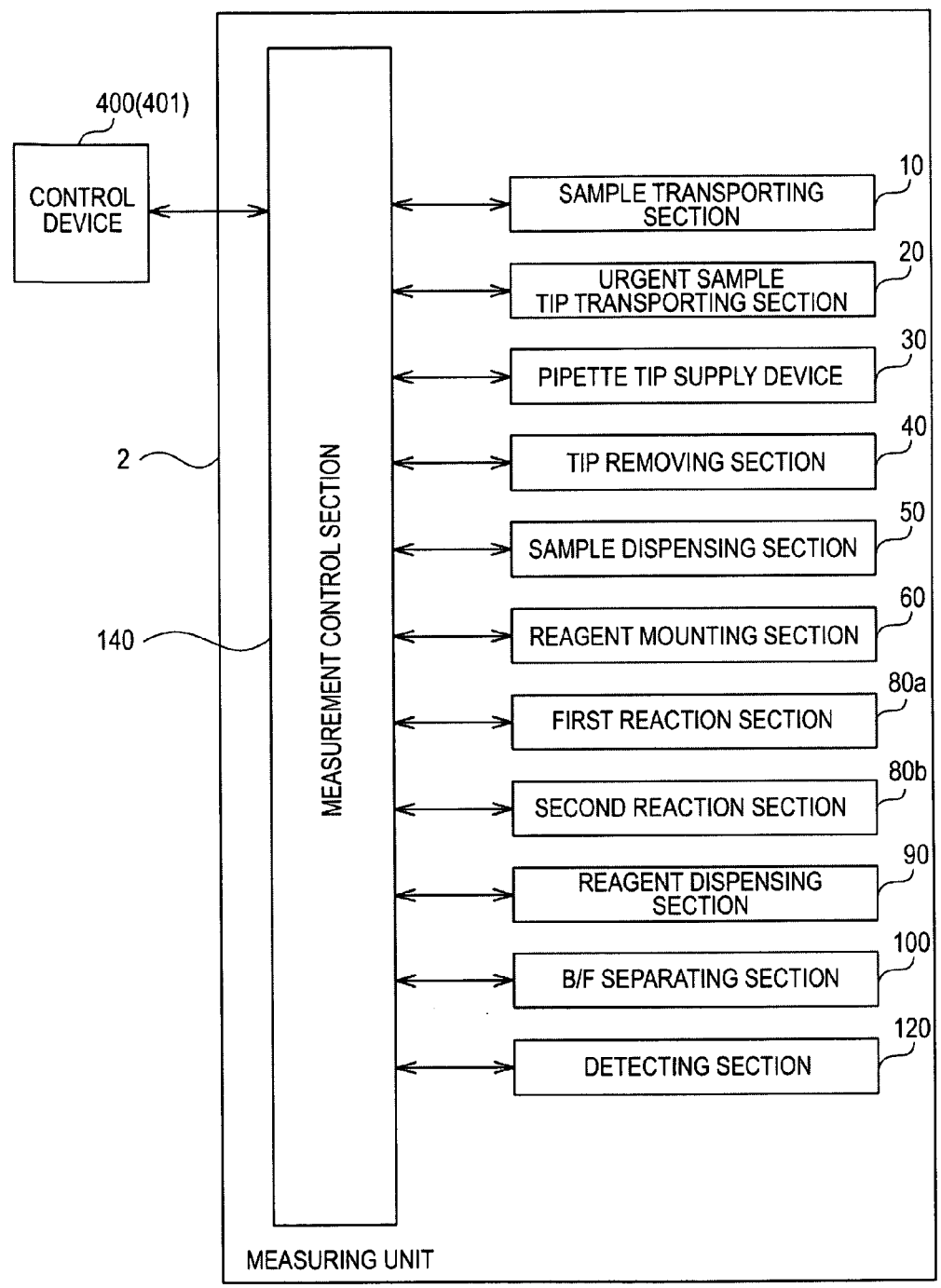
FIG. 2 is a block diagram illustrating the configuration of a measuring unit of the immunological analyzer illustrated in FIG. 1.

FIG. 1 is a plan explanatory diagram illustrating the overall configuration of an immunological analyzer (sample analyzer) according to an embodiment of the invention and FIG. 2 is a block diagram illustrating the configuration of a measuring unit of the immunological analyzer illustrated in FIG. 1.

The immunological analyzer 1 according to an embodiment of the invention is a device for inspecting various measuring items such as hepatitis B, hepatitis C, tumor marker, and thyroid hormone by using a sample (specimen) such as blood. As schematically illustrated in FIG. 1, the immunological analyzer 1 is mainly configured by a measuring unit (measuring section) 2 including a plurality of mechanisms and a control device 400 as a data processing unit which is electrically connected to the measuring unit 2.

The measuring unit 2 has a sample transporting section (sampler) 10, an urgent sample•tip transporting section 20, a pipette tip supply device 30, a tip removing section 40, a sample dispensing section 50, a reagent mounting section (60a and 60b) 60, first and second reaction sections 80a and 80b, a reagent dispensing section (90a to 90e) 90, a B/F separating section (100a and 100b) 100, a detecting section 120 and a measurement control section (see FIG. 2 for reference) 140 for controlling operations of the mechanisms such as the sample transporting section (sampler) 10 and the sample dispensing section 50. In the immunological analyzer 1 according to this embodiment, a disposable pipette tip is exchanged for every suction and ejection of the sample to control mixing of the sample such as blood suctioned and emitted by the sample dispensing section 50 with another sample.

With the immunological analyzer 1, capture antibodies (reagent R1) bound to antigens included in the sample such as blood as a measuring target (analysis target) are bound to magnetic particles (reagent R2) and then the bound antigens, capture antibodies and magnetic particles are drawn to a magnet of the first B/F (Bound Free) separating section 100a to remove the reagent R1 including the unreacted (free) capture antibodies. In addition, after the antigens to which the magnetic particles are bound and labeled antibodies (reagent R3) are bound to each other, the bound magnetic particles, antigens and labeled antibodies are drawn to a magnet of the second B/F separating section 100b to remove the reagent R3 including the unreacted (free) labeled antibodies. Further, luminescent substrates (reagent R5) emitting light in the course of the reaction with a dispersion liquid (reagent R4) or the labeled antibodies are added and then an amount of luminescence generated by the reaction of the labeled antibodies with the luminescent substrates is measured. Through such a course, the antigens included in the sample bound to the labeled antibodies are quantitatively-measured.

[Configuration of Measuring Unit]

The mechanisms of the measuring unit 2 can properly employ known configurations. However, hereinafter, the configurations thereof will be simply described with reference to FIGS. 1 to 3.

Figure 3:
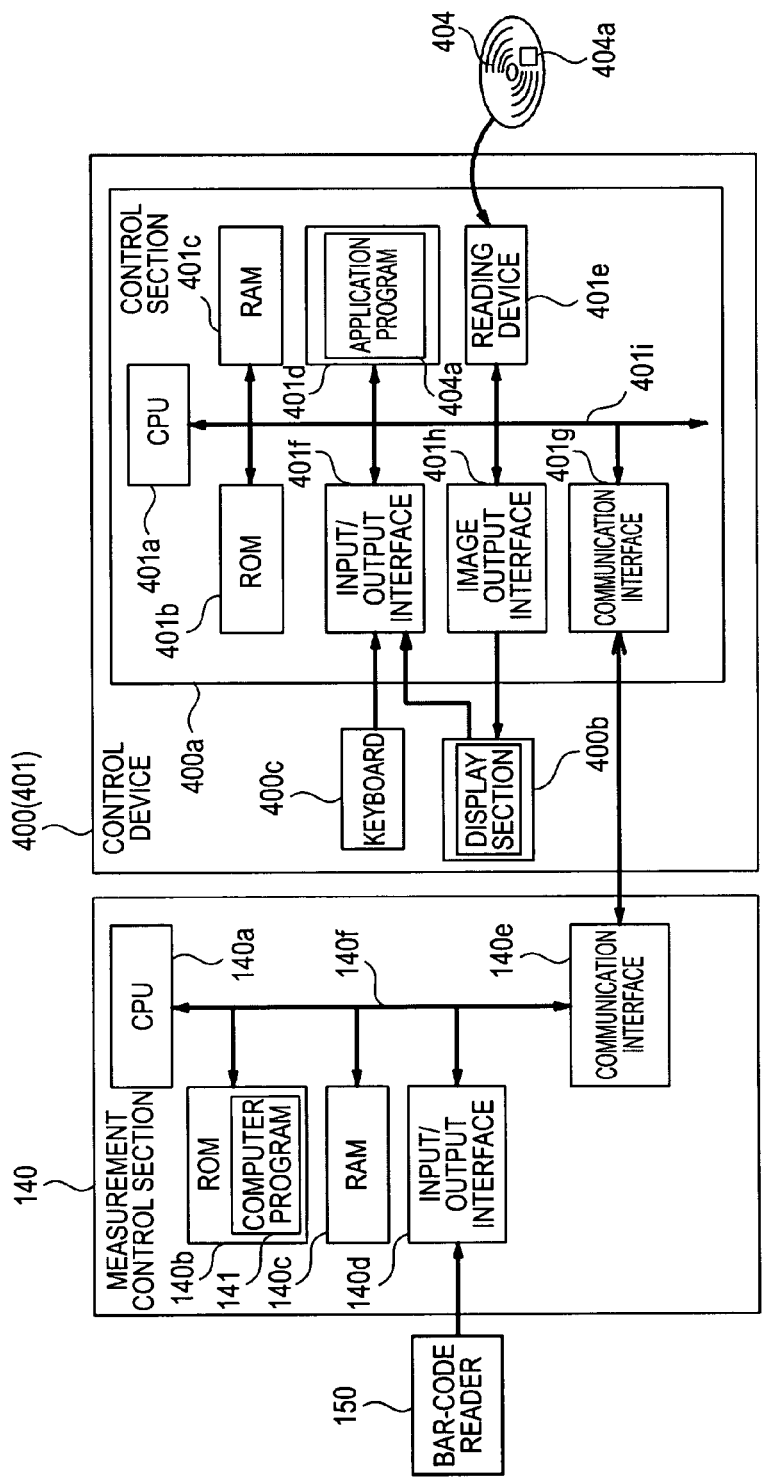
FIG. 3 is a block diagram illustrating the configurations of a measurement control section and a control device of the immunological analyzer illustrated in FIG. 1.

As illustrated in FIG. 3, the measurement control section 140 is mainly configured by a CPU 140a, a storage section including a ROM 140b and a RAM 140c, an input/output interface 140d and a communication interface 140e. The CPU 140a, ROM 140b, RAM 140c, input/output interface 140d and communication interface 140e are connected to each other by a bus 140f.

The CPU 140a can execute a computer program 141 stored in the ROM 140b and a computer program loaded to the RAM 140c.

The ROM 140b includes a mask ROM, a PROM, an EPROM and an EEPROM and a computer program to be executed on the CPU 140a and data to be used for the computer program are recorded therein.

The RAM 140c includes a SRAM and a DRAM. The RAM 140c is used to read computer programs recorded in the ROM 140b. Moreover, the RAM 140c is used as a work area of the CPU 140a when the computer programs are executed.

The input/output interface 140d includes, for example, a serial interface such as USB, IEEE1394 and RS-232C, a parallel interface such as SCSI, IDE, and IEEE1284, and an analog interface including a D/A converter and an A/D converter. A bar-code reader 150 is connected to the input/output interface 140d. To a test tube 3 (see FIG. 1 for reference) containing the sample and a rack 4 (see FIG. 1 for reference) on which a plurality of the test tubes 3 are placed, bar-codes in which information for specifying the sample in the test tube 3 or the rack 4 is recorded are adhered. The bar-code reader 150 is used to read the bar-codes adhered to the test tube 3 and the rack 4.

The communication interface 140e is, for example, an Ethernet (registered trade name) interface. Through the communication interface 140e, the measurement control section 140 can send and receive data to and from a computer 401 by using a predetermined communication protocol.

As shown in FIGS. 1 and 2, the sample transporting section 10 is configured so as to transport the rack 4 on which the plurality of the test tubes 3 containing the samples are placed to a position corresponding to a suction position of the sample dispensing section 50. The sample transporting section 10 has a rack setting section 10a for setting the rack 4 on which the test tube 3 containing the unprocessed sample is placed and a rack storing section 10b for storing the rack 4 on which the test tube 3 containing the sample after dispensing is placed. By transporting the test tube 3 containing the unprocessed sample to the position corresponding to the suction position of the sample dispensing section 50, the sample such as blood in the test tube 3 is suctioned by the sample dispensing section 50 and the rack 4 on which the test tube 3 is placed is stored in the rack storing section 10b.

The urgent sample•tip transporting section 20 is configured so as to transport the test tube 3 containing an urgent sample requiring to be inspected by entering into the sample transported by the sample transporting section 10 to a mounting position of the sample dispensing section 50.

The pipette tip supply device 30 has a function of placing a one put pipette tip on a tip mounting section 23a of a transporting rack 23 of the urgent sample•tip transporting section 20.

The tip removing section 40 is provided to remove the pipette tip mounted on the sample dispensing section 50 to be described later.

The sample dispensing section 50 has a function of dispensing the sample in the test tube 3 transported to the suction position by the sample transporting section 10 into a cuvette (not shown) held in a holding section 81a of a first reaction table 81 of the first reaction section 80a to be described later. The sample dispensing section 50 is configured so as to rotate an arm section 51 around a shaft 52 and move it in an up-and-down direction. Further, a nozzle section for suctioning and ejecting the sample is provided at a tip end of the arm section 51. A tip end of the nozzle section is mounted with the tip of the pipette transported by a transporting rack (not shown) of the urgent sample•tip transporting section 20.

The reagent mounting section 60a is a rotation table which is rotated and driven. On this section, a reagent container 201 for containing the reagent R1 including the capture antibodies and a reagent container 202 for containing the reagent R3 including the labeled antibodies are mounted.

In addition, the reagent mounting section 60b is a rotation table which is rotated and driven. On this section, a reagent container for containing the reagent R2 including the magnetic particles is mounted.

The first reaction section 80a is provided to rotate and move by a predetermined angle at predetermined intervals (in this embodiment, 20 seconds) the cuvette held in the holding section 81a of the first reaction table 81 which is rotated and driven and to stir the reagents R1 and R2 and the sample in the cuvette. That is, the first reaction section 80a is provided to react the reagent R2 having the magnetic particles with the antigens in the sample in the cuvette. The first reaction section 80a is configured by the first reaction table 81 and a container transporting section 82. The first reaction table 81 transports the cuvette containing the sample and the reagents R1 and R2 in a rotation direction. The container transporting section 82 stirs the sample and the reagents R1 and R2 in the cuvette 8 and transports the cuvette containing the stirred sample and reagents R1 and R2 to the first B/F separating section 100a to be described later.

The container transporting section 82 is rotatably mounted at the center of the first reaction table 81. The container transporting section 82 has a function of grasping the cuvette held in the holding section 81a of the first reaction table 81 and stirring the specimen in the cuvette. In addition, the container transporting section 82 also has a function of transporting the cuvette containing the specimen resulting from stirring and incubating the sample and the reagents R1 and R2 to the first B/F separating section 100a.

The reagent dispensing section 90a has a function of suctioning the reagent R1 in the reagent container mounted on the reagent mounting section 60a and dispensing the suctioned reagent R1 into the cuvette of the first reaction section 80a. The reagent dispensing section 90a has a driving section (see FIG. 5 for reference) 160 capable of rotating an arm section 91b around a shaft 91c and moving it in an up-and-down direction. A pipette P (see FIG. 5 for reference) for suctioning and ejecting the reagent R1 in the reagent container 201 is attached to a tip end of the arm section 91b. Further, the reagent dispensing section 90a has a collision detecting sensor (see FIG. 6 for reference) 170 for use in detecting collision of the pipette P with an obstacle. The driving section 160 constitutes a pipette moving mechanism for moving a tip end of the pipette P to a predetermined position (position of a position confirming member 210 (see FIG. 5 for reference)) as described below.

Figure 5:
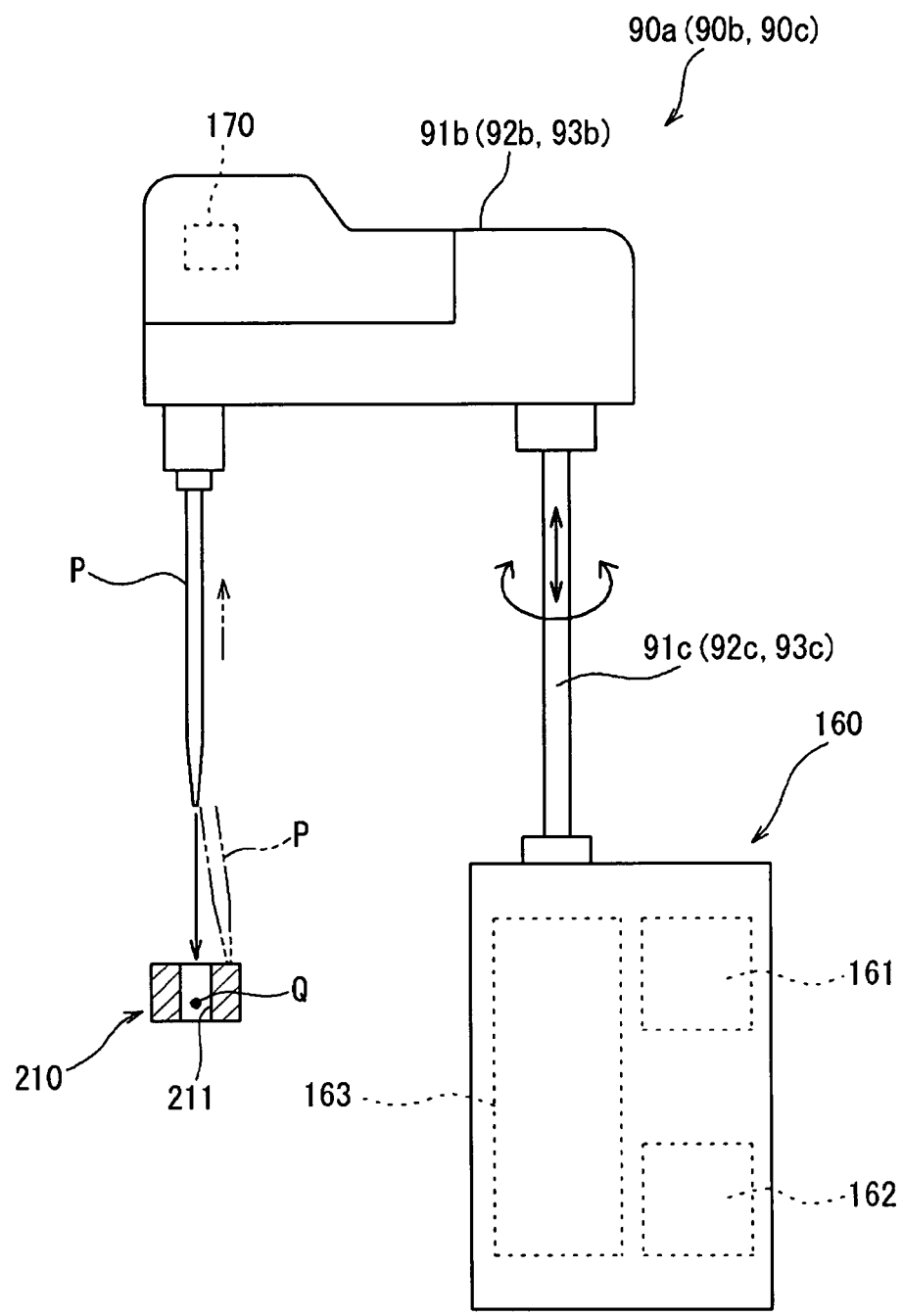
FIG. 5 is a side view schematically illustrating the configuration of a reagent dispensing section of the immunological analyzer illustrated in FIG. 1.

FIG. 5 is a side view schematically illustrating the configuration of the reagent dispensing section. As illustrated in this drawing, the driving section 160 has a rotating motor 161, a lifting motor 162, and a transmission mechanism 163 for transmitting power of the rotating motor 161 and the lifting motor 162 to the shaft 91c. For example, the transmission mechanism 163 includes a belt transmission mechanism, a gear mechanism and the like for decelerating rotation power of the rotating motor 161 to transmit the decelerated rotation power to the shaft 91c and a belt transmission mechanism, a rack and pinion mechanism and the like for converting rotation power of the lifting motor 162 into linear power in an up-and-down direction to transmit the converted power to the shaft 91c. Rotation pulses of the rotating motor 161 and the lifting motor 162 are detected by an encoder (omitted).

Figure 6:
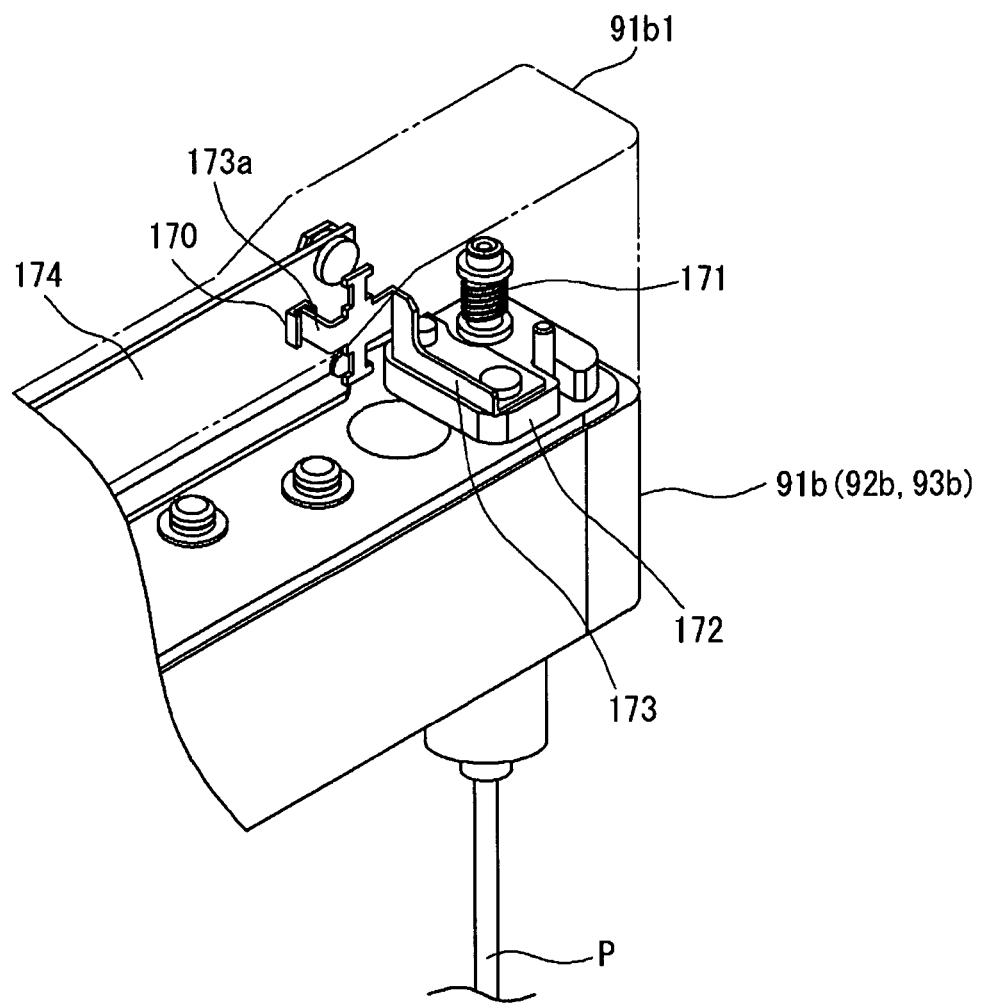
FIG. 6 is a perspective view illustrating an arm section and a collision detecting sensor of the immunological analyzer illustrated in FIG. 1.

FIG. 6 is a perspective view illustrating the arm section 91b and the collision detecting sensor 170. In this drawing, the arm section 91b, inside of which is exposed by detaching an upper cover 91b1 (indicated by the chain double-dashed line) is illustrated. The pipette P is supported on the arm section 91b so as to be moved in an up-and-down direction and downward movement of the pipette P is regulated within a predetermined range. Further, the pipette P is urged downward by an urging member 171 including a compression coil spring. The arm section 91b is provided with a base 172 movable together with the pipette P in an up-and-down direction and a sensing member 173 is attached on the base 172. A circuit board 174 is erected on the arm section 91b and the collision detecting sensor 170 is attached to the circuit board 174.

In this embodiment, the collision detecting sensor 170 includes a transmission type sensor having a light projecting section and a light receiving section. The sensing member 173 is provided with a light shielding plate 173a disposed between the light projecting section and the light receiving section of the collision detecting sensor 170. Normally, the light shielding plate 173a shields the light from the collision detecting sensor 170 to switch the collision detecting sensor 170 off. When the pipette P is moved downward and collides with the obstacle, the pipette P is moved upward with respect to the arm section 91b and the light shielding plate 173a is also moved upward through the base 172. Accordingly, the shielding of the light from the collision detecting sensor 170 is released. In this manner, when the collision detecting sensor 170 is switched on, the collision of the pipette P with the obstacle is detected by the measurement control section 140.

As illustrated in FIG. 1, the reagent dispensing section 90b has a function of dispensing the reagent R2 in the reagent container mounted on the reagent mounting section 60b into the cuvette into which the sample and the reagent R1 of the first reaction section 80a are dispensed. The reagent dispensing section 90b is configured so as to rotate an arm section 92b around a shaft 92c and move it in an up-and down direction. Further, a pipette P for suctioning and ejecting the reagent R2 in the reagent container is attached to a tip end of the arm section 92b. As in the case of the reagent dispensing section 90a, the reagent dispensing section 90b has a driving section 160 and a collision detecting sensor 170 as shown in FIGS. 5 and 6.

In this embodiment, the first B/F separating section 100a is provided to separate the unreacted reagent R1 (unnecessary components) and the magnetic particles from the specimen in the cuvette transported by the container transporting section 82 of the first reaction section 80a.

The cuvette of the first B/F separating section 100a from which the unreacted reagent R1 and the like are separated is transported to a holding section 83a of a second reaction table 83 of the second reaction section 80b by a transporting mechanism 96. The transporting mechanism 96 is configured so as to rotate an arm section 96a having a cuvette grasping section (not shown) at a tip end thereof around a shaft 96b and move it in an up-and-down direction.

The second reaction section 80b has the same configuration as the first reaction section 80a and is provided to rotate and move by a predetermined angle at predetermined intervals (in this embodiment, 20 seconds) the cuvette held in the holding section 83a of the second reaction table 83 and to stir the reagents R1, R2, R3, R4 and R5 and the sample in the cuvette. That is, the second reaction section 80b is provided to react the reagent R3 having the labeled antibodies with the antigens in the sample and to react the reagent R5 having the luminescent substrates with the labeled antibodies of the reagent R3 in the cuvette. The second reaction section 80b is configured by the second reaction table 83 for transporting the cuvette 8 containing the sample and the reagents R1, R2, R3, R4 and R5 in a rotation direction and a container transporting section 84 for stirring the reagents R1, R2, R3, R4 and R5 and the sample in the cuvette and transporting the cuvette containing the stirred sample and the like to the second B/F separating section 100b to be described later. The container transporting section 84 has a function of transporting the cuvette processed by the second B/F separating section 100b to the holding section 83a of the second reaction table 83 again.

The reagent dispensing section 90c has a function of suctioning the reagent R3 in the reagent container 202 mounted on the reagent mounting section 60a and dispensing the suctioned reagent R3 into the cuvette into which the reagents R1 and R2 and the sample of the second reaction section 80b are dispensed. The reagent dispensing section 90c is configured so as to rotate an arm section 93b around a shaft 93c and move it in an up-and down direction. Further, a pipette P for suctioning and ejecting the reagent R3 in the reagent container is attached to a tip end of the arm section 93b. As in the case of the reagent dispensing section 90a, the reagent dispensing section 90c has a driving section 160 and a collision detecting sensor 170 as illustrated in FIGS. 5 and 6.

The second B/F separating section 100b has the same configuration as the first B/F separating section 100a and is provided to separate the unreacted reagent R3 (unnecessary components) and the magnetic particles from the reagent in the cuvette transported by the container transporting section 84 of the second reaction section 80b.

The reagent R4 dispensing section 90d and the reagent R5 dispensing section 90e are provided to move a nozzle section (not shown) in an up-and-down direction to thereby supply the reagent R4 and the reagent R5 to the cuvette held in the second reaction table 83 of the second reaction section 80b.

The detecting section 120 is provided to obtain an amount of luminescence generated in the course of the reaction of the luminescent substrates with the labeled antibodies bound to the antigens of the sample subjected to a predetermined process by a photomultiplier tube to thereby measure an amount of the antigens included in the sample. The detecting section 120 has a transporting mechanism section 121 for transporting the cuvette held in the holding section 83a of the second reaction table 83 of the second reaction section 80b to the detecting section 120.

In addition to the above-mentioned configuration, the measuring unit 2 according to this embodiment has pipette cleaning sections 220 for cleaning the pipettes P of the reagent dispensing sections 90a to 90c and the position confirming members 210 for confirming positions of the tip ends of the pipettes P as illustrated in FIG. 1. Hereinafter, a description will be given with respect to the position confirming member 210 and the pipette cleaning section 220 for the reagent dispensing section 90a. Since the position confirming members 210 and the pipette cleaning sections 220 for the reagent dispensing sections 90b and 90c have the same configurations, descriptions thereof will be omitted.

(Configuration of Pipette Cleaning Section)

Figure 7:
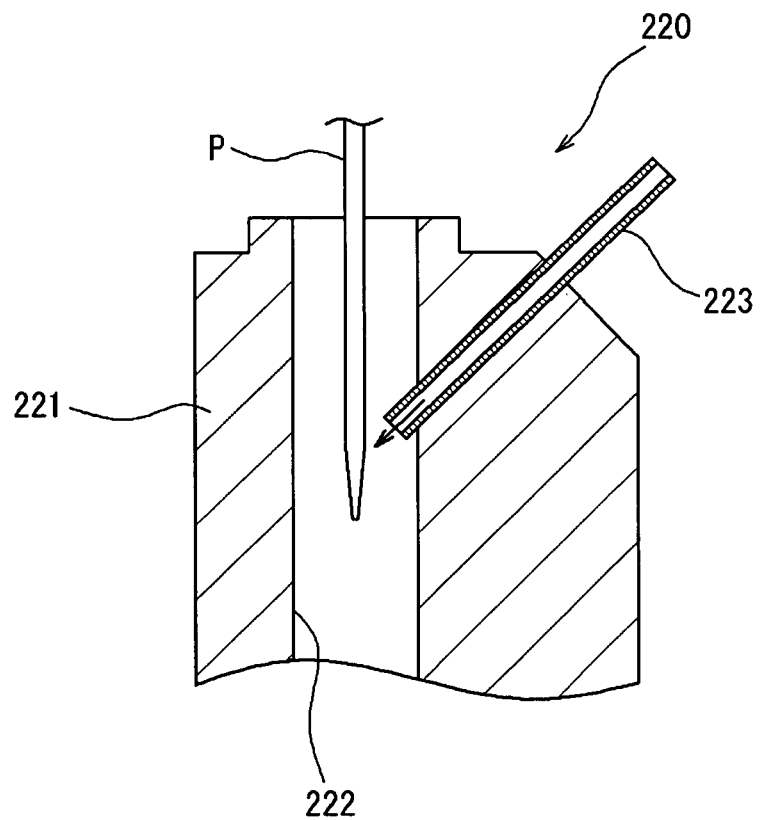
FIG. 7 is a cross-sectional view illustrating a pipette cleaning section of the immunological analyzer illustrated in FIG. 1.

As illustrated in FIG. 7, the pipette cleaning section 220 has a cleaning container 221 and the cleaning container 221 is provided with a cleaning hole 222 for inserting the pipette P therethrough and a cleaning nozzle 223 for ejecting a cleaning liquid into the cleaning hole 222. The cleaning hole 222 is open at an upper end of the cleaning container 221 and the pipette P can be inserted from this opening. The cleaning nozzle 223 is configured so as to clean the pipette P by ejecting the cleaning liquid to the cleaning hole 222 from the obliquely upper side and thereby spraying the cleaning liquid to the pipette P inserted into the cleaning hole 222.

As illustrated in FIG. 1, in plan view, the pipette cleaning section 220 is disposed on a moving locus (rotation locus around the shaft 91c; see the arrow for reference) of the pipette P of the reagent dispensing section 90a. In addition, the pipette cleaning section 220 is disposed at a predetermined distance away from an origin position (for example, position of the arm section 91b illustrated in FIG. 1) of the arm section 91b of the reagent dispensing section 90a in a horizontal direction and a downward direction. Accordingly, by rotating the arm section 91b of the reagent dispensing section 90a from the origin position to an upper position of the pipette cleaning section 220 by a predetermined distance and moving the arm section 91b downward, the pipette P can be inserted into the cleaning hole 222 of the cleaning container 221.

(Configuration of Position Confirming Member)

Figure 9:
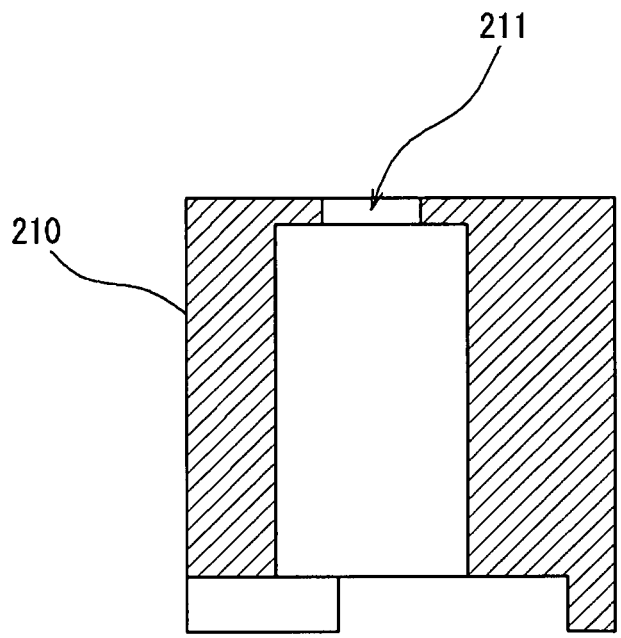
FIG. 9 is a diagram illustrating an example of the position confirming member illustrated in FIG. 5.

The position confirming member 210 is used to confirm whether the pipette P of the reagent dispensing section 90a has been accurately disposed at a predetermined position when the pipette P has moved to the predetermined position. As illustrated in FIG. 5, the position confirming member 210 is formed in a block shape having a hole (space) 211 penetrating therethrough in an up-and-down direction. The hole 211 has a diameter slightly larger (about 2 mm) than an outer diameter of the pipette P such that the pipette P can be inserted therethrough with a small gap (gap of about 1 mm in radius). The hole 211 may be a hole with a bottom not penetrating through the position confirming member 210. As illustrated in FIG. 9, the hole 211 may have a diameter slightly larger than the outer diameter of the pipette P at an upper end thereof such that the pipette P can be inserted therethrough with a small gap (gap of about 1 mm in radius), and may have a diameter at the other part thererof such that the pipette P can be inserted therethrough with a sufficient gap. By forming the hole in such a shape, position confirmation accuracy of the position confirming member 210 can be maintained and the probability that the pipette P is contaminated by the reagent and the cleaning liquid sticking to an inner wall surface of the hole 211 can be reduced.

As illustrated in FIG. 1, in plan view, the position confirming member 210 is disposed on the moving locus (rotation locus around the shaft 91c; see the arrow for reference) of the pipette P of the reagent dispensing section 90a. In addition, the position confirming member 210 is disposed at a predetermined distance away from the origin position (for example, position of the arm section 91b illustrated in FIG. 1) of the arm section 91b of the reagent dispensing section 90a in a horizontal direction and a downward direction. Accordingly, by rotating the arm section 91b from the origin position to an upper position of the position confirming member 210 by a predetermined distance and moving the arm section 91b downward, the tip end of the pipette P can be inserted into the hole 211 of the position confirming member 210.

The pipette P is disposed at a position having a possibility of being touched by a user in the measuring unit 2. For this reason, the user may touch the pipette P by mistake and the pipette P may be thereby bent. Moreover, due to elongation of the belt used for a long period of time, the driving section 160 of the reagent dispensing section 90a may not accurately stop the tip end of the pipette P at a predetermined position. When such problems (problems of the pipette P in shape and operation) are generated, the tip end of the pipette P cannot be inserted into the hole 211 of the position confirming member 210 and thus the tip end of the pipette P collides with the position confirming member 210 as indicated by the chain double-dashed line of FIG. 5.

As described above, the arm section 91b according to this embodiment is provided with the collision detecting sensor 170. Accordingly, when the tip end of the pipette P collides with the position confirming member 210, the measurement control section 140 can detect the collision. In other words, it is possible to detect whether the tip end of the pipette P has been disposed at a predetermined position (in the hole 211) on the basis of an output of the collision detecting sensor 170 by the measurement control section 140. In this embodiment, the position confirming member 210 and the collision detecting sensor 170 constitute position confirming means for confirming whether the tip end of the pipette P has been disposed at a predetermined position.

[Configuration of Control Device]

The control device 400 includes a personal computer (PC) 401 and the like. As illustrated in FIG. 1, the control device has a control section 400a, a display section 400b and an input section (input means) 400c such as a keyboard or a mouse. The control section 400a has a function of controlling operations of the mechanisms in the measuring unit 2 and analyzing optical information of the sample obtained by the measuring unit 2. The control section 400a includes a CPU, a ROM, a RAM and the like. The display section 400b is used to display information about the analysis result obtained by the control section 400a.

Next, the configuration of the control device 400 will be described. As illustrated in FIG. 3, the control section 400a is mainly configured by a CPU 401a, a storage section including a ROM 401b, a RAM 401c and a hard disk 401d and the like, a reading device 401e, an input/output interface 401f, a communication interface 401g, and an image output interface 401h.

The CPU 401a, ROM 401b, RAM 401c, hard disk 401d, reading device 401e, input/output interface 401f, communication interface 401g, and image output interface 401h are connected to each other by a bus 401i.

The CPU 401a can execute a computer program stored in the ROM 401b and a computer program loaded to the RAM 401c. The computer 401 functions as the control device 400 by executing an application program 404a to be described later on the CPU 401a.

The ROM 401b includes a mask ROM, a PROM, an EPROM and an EEPROM and a computer program to be executed on the CPU 401a and data to be used for the computer program are recorded therein.

The RAM 401c includes a SRAM and a DRAM. The RAM 401c is used to read computer programs recorded in the ROM 401b and the hard disk 401d. Moreover, the RAM 140c is used as a work area of the CPU 401a when the computer programs are executed.

On the hard disk 401d, various computer programs 404a for being executed on the CPU 401a, such as an operating system and an application program, and data to be used for the computer programs are installed. For example, an application program for registering a measuring order and an application program for controlling the operation of the measuring unit 2 are installed on the hard disk 401d.

The reading device 401e includes a flexible disk drive, a CD-ROM drive, and a DVD-ROM drive to read a computer program or data recorded in a portable recording medium 404. The portable recording medium 404 stores the application program 404a according to this embodiment and the computer 401 reads the application program 404a from the portable recording medium 404 to install the application program 404a on the hard disk 401d.

Further, the application program 404a can be not only provided by the portable recording medium 404 but also provided from an exterior device communicatably connected to the computer 401 by an electrical communication line (both wired and wireless) through the electrical communication line. For example, the application program 404a can be stored in a hard disk of a server computer on the internet and the computer 401 can access the server computer to download the application program 404a and then the downloaded application program can be installed on the hard disk 401d.

For example, on the hard disk 401d, an operating system to provide a graphical user interface environment such as Windows (registered trade name) made and distributed by Microsoft corporation, America, is installed. In the following description, the application program 404a according to this embodiment operates on the above-mentioned operating system.

The input/output interface 401f includes, for example, a serial interface such as USB, IEEE1394 and RS-232C, a parallel interface such as SCSI, IDE, and IEEE1284, and an analog interface including a D/A converter and an A/D converter. The keyboard 400c is connected to the input/output interface 401f. A user uses the keyboard 400c to input data to the computer 401.

The communication interface 401g is, for example, an Ethernet (registered trade name) interface. Through the communication interface 401g, the computer 401 can send and receive data to and from the measuring unit 2 by using a predetermined communication protocol.

The image output interface 401h is connected to the display section 400b including LCD and CRT to output a picture signal responding to image data given from the CPU 401a to the display section 400b. The display section 400b displays an image (screen) in accordance with the input picture signal.

[Overall Process of Analysis which is Performed by Immunological Analyzer]

Figure 4:
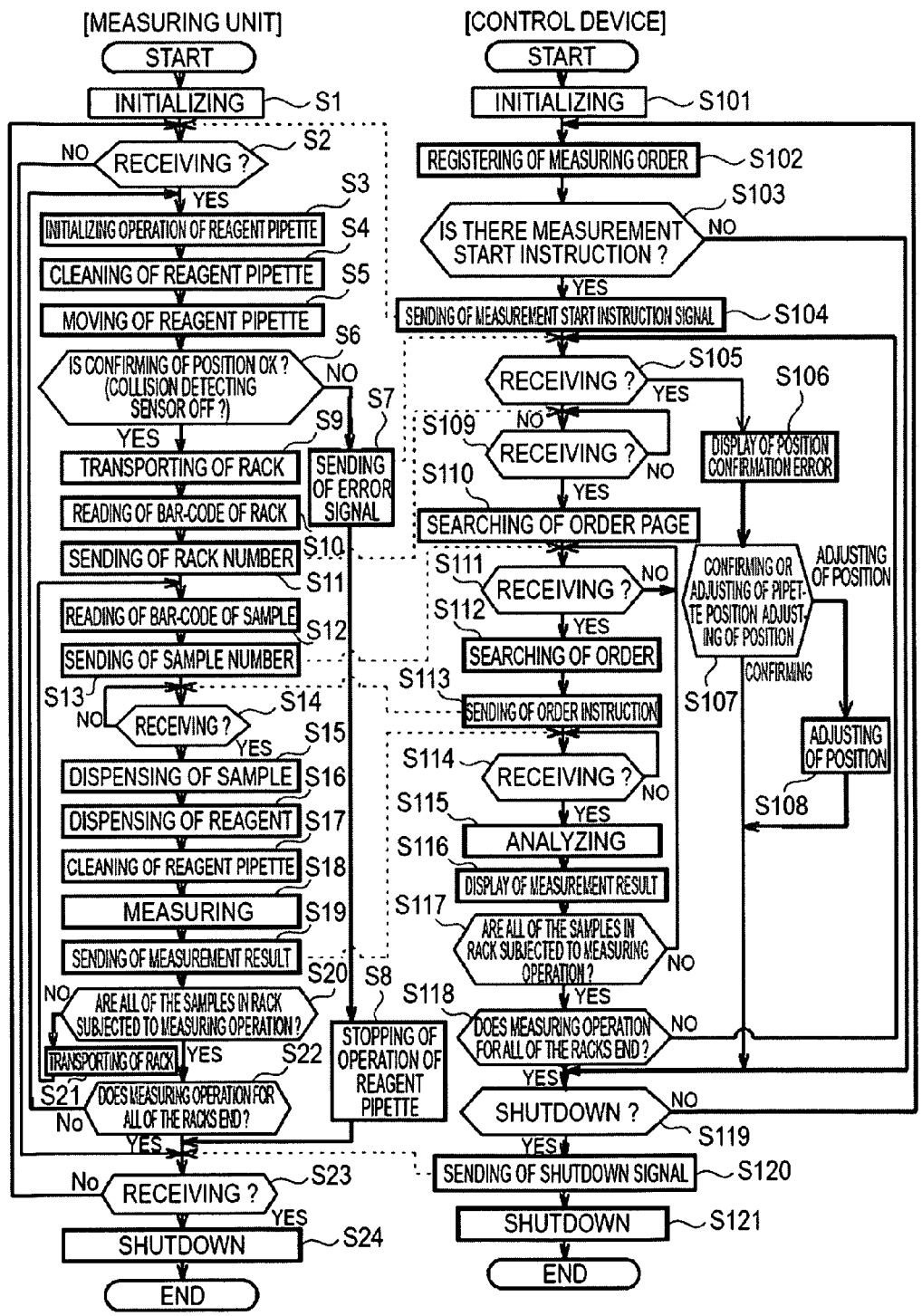
FIG. 4 is a diagram illustrating the overall flow of analysis of the immunological analyzer illustrated in FIG. 1.

FIG. 4 illustrates the overall flow of the analysis which is performed by the immunological analyzer 1. Hereinafter, the overall analysis which is performed by the immunological analyzer 1 will be described. In the following description, "process" is a process controlled by the control section 400a of the control device 400 or the measurement control section 140 of the measuring unit 2.

Firstly, when the immunological analyzer 1 is turned on, initialization of the measurement control section 140 is performed (Step S1). In this initializing operation, program initialization, returning of the driving section of the immunological analyzer 1 to the origin position and the like are performed.

Meanwhile, when the control device 400 communicatably connected to the immunological analyzer 1 is turned on, initialization of the control section 400a of the control device 400 is performed (Step S101). In this initializing operation, program initialization and the like are performed.

When the initialization of the measurement control section 140 and the control device 400 ends, the immunological analyzer 1 is kept in a state in which it is ready to start measurement (analysis) (standby state).

Next, in Step S102, an order of the samples to be analyzed by the immunological analyzer 1 is registered (Step S102). In this order registration, for example, information such as sample numbers or measuring items (analysis items) is input from the keyboard (input means) 400c by a user, and then after confirming the content, the user clicks an instruction button for the order registration. The order registration performed by the control section 400a is stored in a storage area of the hard disk 401d.

Figure 8:
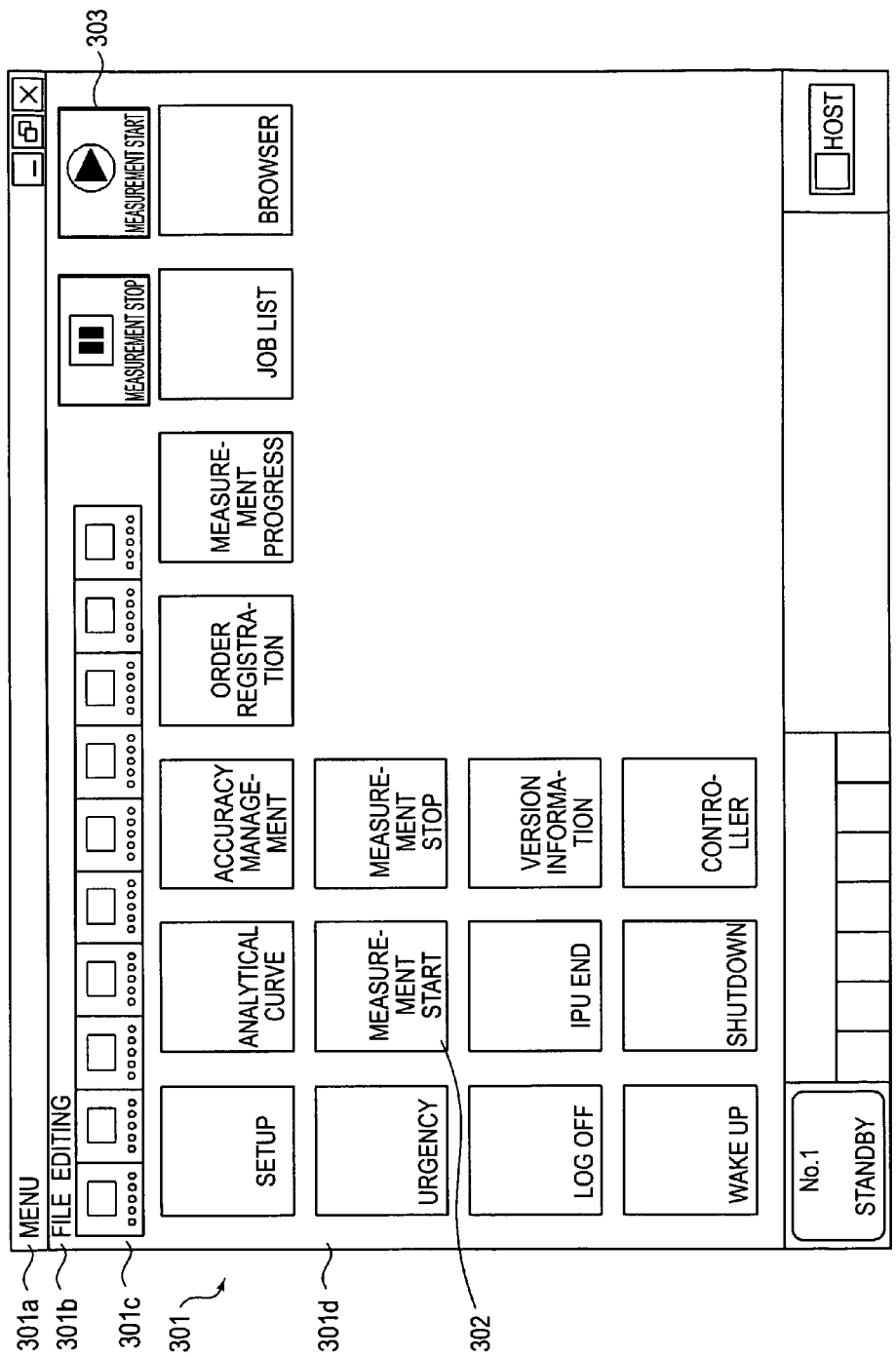
FIG. 8 is a diagram illustrating a menu screen displayed on a display section of the immunological analyzer illustrated in FIG. 1.

Next, in Step S103, determining whether a measurement start instruction has been received is performed by the control section 400a. FIG. 8 is a diagram illustrating a menu screen 301 displayed on the display section 400b of the control device 400 in the standby state. In the menu screen 301, a title bar 301a, a menu bar 301b, a tool bar 301c and a main display section 301d are displayed. "Measurement start" buttons 303 and 302 are provided in the tool bar 301c and the main display section 301d. The measurement (analysis) start instruction can be given to the immunological analyzer 1 by pressing (clicking) the "measurement start" buttons 303 and 302.

When the control section 400a determines that the measurement start instruction has been received (Yes), the process proceeds to Step S104. When the control section 400a determines that the measurement start instruction has not been received (No), the process proceeds to Step S119. In Step S104, the control section 400a sends a measurement start signal to the measurement control section 140.

Next, in Step S2, determining whether the measurement start signal has been received is performed by the measurement control section 140. When the measurement control section 140 determines that the measurement start signal has been received (Yes), the process proceeds to Step S3. When the measurement control section 140 determines that the measurement start signal has not been received (No), the process proceeds to Step S23.

In Step S3, the measurement control section 140 performs initializing operations of the pipettes P of the reagent dispensing sections 90a to 90c, that is, operations for returning the pipettes P to the origin positions thereof. Then, the process proceeds to Step S4.

In Step S4, cleaning for the pipettes P of the reagent dispensing sections 90a to 90c is performed. Specifically, as illustrated in FIG. 7, the pipettes P of the reagent dispensing sections 90a to 90c are inserted into the cleaning containers 221 and then the cleaning liquid ejected from the cleaning nozzles 222 is sprayed to the pipettes P.

Next, in Step S5, the pipettes P of the reagent dispensing sections 90a to 90c are moved. Specifically, as illustrated in FIG. 5, the pipette P is moved to the upper position of the position confirming member 210 by the driving section 160 and then is moved downward. The tip end of the pipette P is inserted into the hole 211 of the position confirming member 210. In this manner, the tip end of the pipette P is disposed at a confirmation position Q.

In Step S6, when the tip end of the pipette P is inserted into the hole 211 of the position confirming member 210, the measurement control section 140 determines whether the pipette P has collided with the position confirming member 210 on the basis of an output of the collision detecting sensor 170 to confirm that the tip end of the pipette P reaches the confirmation position Q. Specifically, in case where the tip end of the pipette P is inserted into the hole 211 of the position confirming member 210, it is determined that the tip end of the pipette P reaches the confirmation position Q when the collision detecting sensor 170 does not change in output without sensing anything (that is, when light from the collision detecting sensor 170 is shielded by the light shielding plate 173a), and it is determined that the pipette P collides with the position confirming member 210 and the tip end of the pipette P does not reach the confirmation position Q when the collision detecting sensor 170 changes in output without sensing anything (that is, when light shielding of the light shielding plate 173a for the collision detecting sensor 170 is released to switch the collision detecting sensor 170 on). When the measurement control section 140 determines that the tip end of the pipette P has reached the confirmation position Q in the hole 211 of the position confirming member 210 (Yes), the process proceeds to Step S9. When the measurement control section 140 determines that the tip end of the pipette P has not been inserted so as to reach the confirmation position Q in the hole 211 of the position confirming member 210 (No), the process proceeds to Step S7.

In Step S7, by the measurement control section 140, a signal indicating a position confirmation error of the pipette P is sent to the control device 400 and the process proceeds to Step S8.

Next, in Step S8, the measurement control section 140 moves the pipette P to an upper limit position and then stops the pipette P and the overall operation of the device. After that, the process proceeds to Step S23.

In Step S105, determining whether the error signal has been received is performed by the control section 400a. When the control section 400a determines that the error signal has been received (Yes), the process proceeds to Step S106. When the control section 400a determines that the error signal has not been received (No), the process proceeds to Step S109.

In Step S106, by the control section 400a, the position confirmation error of the pipette P is displayed on the display section 400b. For example, the error display shows that the pipette P is bent or has a problem in movement, or that exchange with a new pipette P is required. The user sees the error display and thus recognizes that the shape or the operation of the pipette P has a problem. In this manner, measures such as exchange of the pipette P can be performed. The error display includes a confirmation button for returning the device state to a standby state and a pipette position adjustment button for performing position adjustment of the pipette.

Next, in Step S107, determining whether the confirmation button has been selected or the pipette position adjustment button has been selected is performed by the control section 400a. When the confirmation button is selected, the process proceeds to Step S119 and the device returns to a standby state. When the pipette position adjustment button is selected in Step S107, the position of the pipette is adjusted in Step S108.

Next, in Step S9, the rack 4 on which the plurality of the test tubes 3 containing the samples are placed is transported to a position corresponding to the suction position of the sample dispensing arm 50 by the sample transporting section 10. A bar-code in which information (rack number) for specifying the rack 4 is recorded is adhered to the rack 4 and is read (Step S10) by the bar-code reader (see FIG. 3 for reference) 150 provided in the transport path for transporting the rack 4 to a predetermined position. The read rack number is sent to the control device 400 by the measurement control section 140 in Step S11.

Next, in Step S109, determining whether the rack number has been received is performed by the control section 400a. When the control section 400a determines that the rack number has been received (Yes), the process proceeds to Step S110.

Next, in Step S110, searching of an order page is performed by the control section 400a. That is, from order information stored in the storage area of the hard disk 401d, the control section 400a searches the order information related to the rack number received in Step S109.

As in the case of the rack 4, a bar-code in which information (sample number) for specifying the sample in the test tube 3 is recorded is adhered to the test tube 3 and is read (Step S12) by the bar-code reader (see FIG. 3 for reference) 150 provided in the transport path for transporting the rack 4 on which the test tube 3 is placed to a predetermined position. In Step S13, the measurement control section 140 sends the read sample number to the control device 400. The bar-codes of the test tube 3 and the rack 4 may be read by different bar-code readers or by a common bar-code reader.

Next, in Step S111, determining whether the sample number has been received is performed by the control section 400a. When the control section 400a determines that the sample number has been received (Yes), the process proceeds to Step S112.

Next, in Step S112, searching of the order is performed by the control section 400a. That is, from the order information related to the specified rack number searched in Step S110, the control section 400a searches the order information related to the sample number received in Step S111. Then, in Step S113, the control section 400a sends an order instruction to the measurement control section 140.

Next, in Step S14, determining whether the order instruction has been received is performed by the measurement control section 140. When the measurement control section 140 determines that the order instruction has been received (Yes), the process proceeds to Step S15.

Next, in Step S15, the ordered item is subjected to a measuring operation. Specifically, the sample in the test tube 3 is dispensed into the cuvette by the sample dispensing section 50, a predetermined reagent is dispensed into the cuvette by the reagent dispensing section 90a and the like (Step S16), and then a predetermined process is performed in the B/F separating sections 100a and 100b to mix the reagent and the specimen and thus a measuring specimen is prepared. The pipette P after the dispensing of the reagent is cleaned by the pipette cleaning section 220 (Step S17). After that, by the detecting section 120, the measuring specimen is subjected to a predetermined measuring operation (Step S18) and then the measurement result is sent to the control device 400 by the measurement control section 140 (Step S19).

Next, in Step S114, determining whether the measurement result has been received is performed by the control section 400. When the control section 400a determines that the measurement result has been received (Yes), the process proceeds to Step S115.

In Step S115, the measurement result sent from the measurement control section 140 is analyzed. That is, from the sent measurement result and an analytical curve preliminarily created using a standard specimen and stored in the hard disk 401d, the control section 400a computes the concentration of the antigens in the target for measurement and stores the result (analysis result). Further, the control section 400a outputs the analysis result to the display section 400b (Step S116).

Next, in Step S117, determining whether the samples in all of the test tubes 3 held in the rack 4 have been subjected to the measuring operation is performed by the control section 400a. When the control section 400a determines that the samples in all of the test tubes 3 held in the rack 4 have been subjected to the measuring operation (Yes), the process proceeds to Step S118. When the control section 400a determines that the samples in all of the test tubes 3 held in the rack 4 have not been subjected to the measuring operation (No), the process returns to Step S111.

Next, in Step S118, determining whether all of the racks 4 have been subjected to the measuring operation is performed by the control section 400a. When the control section 400a determines that all of the racks 4 have been subjected to the measuring operation (Yes), the process proceeds to Step S119. When the control section 400a determines that all of the racks 4 have not been subjected to the measuring operation (No), the process returns to Step S105.

Next, in Step S119, determining whether an instruction for shutdown of the control device 400 has been received is performed by the control section 400a. When the control section 400a determines that the instruction for shutdown has been received (Yes), the process proceeds to Step S120. When the control section 400a determines that the instruction for shutdown has not been received (No), the process returns to Step S102.

Next, in Step S120, a shutdown signal is sent to the measurement control section 140 from the control section 400a.

Then, in Step S121, shutdown of the control device 400 is performed by the control section 400a and then the process ends.

In addition, in Step S20, determining whether the samples in all of the test tubes 3 held in the rack 4 have been subjected to the measuring operation is performed by the measurement control section 140. When the measurement control section 140 determines that the samples in all of the test tubes 3 held in the rack 4 have been subjected to the measuring operation (Yes), the process proceeds to Step S22. When the measurement control section 140 determines that the samples in all of the test tubes 3 held in the rack 4 have not been subjected to the measuring operation (No), the sample transporting section 10 is controlled (Step S21) so as to transport the rack 4 by a predetermined distance (a distance to a suctioning position from the test tube containing the sample to be subjected to the measuring operation next time) and the process returns to Step S12.

Next, in Step S22, determining whether all of the racks 4 have been subjected to the measuring operation is performed by the measurement control section 140. When the measurement control section 140 determines that all of the racks 4 have been subjected to the measuring operation (Yes), the process proceeds to Step S23. When the measurement control section 140 determines that all of the racks 4 have not been subjected to the measuring operation (No), the process returns to Step S4.

Next, in Step S23, determining whether the shutdown signal has been received is performed by the measurement control section 140. When the measurement control section 140 determines that the shutdown signal has been received (Yes), the process proceeds to Step S24. When the measurement control section 140 determines that the shutdown signal has not been received (No), the process returns to Step S2.

Then, in Step S24, the shutdown of the immunological analyzer 1 is performed by the measurement control section 140 and then the process ends.

In the above-mentioned overall process of the immunological analyzer 1, the position confirming operations (Step S6) of the pipettes P of the reagent dispensing sections 90a to 90c are automatically performed in accordance with a predetermined operation sequence after the control device 400 and the measuring unit 2 are initialized (Steps S1 and S101) and then are ready to start measurement. Accordingly, the user does not have to intentionally perform the position confirming operation of the pipette P and to manage timing at which the position confirmation of the pipette P is performed. Consequently, a burden on the user can be reduced.

Further, the position confirming operations of the pipettes P of the reagent dispensing sections 90a to 90c are performed after the measurement start instruction is received in the control device 400. Accordingly, the position confirming operation of the pipette P is necessarily performed at every measurement (analysis). Consequently, it is possible to prevent that reliability of the measurement result is lowered by insufficient cleaning of the pipette P or a damage of the pipette P through the collision with the reagent container or the like, resulting from a problem of the pipette P (a problem of the pipette P in shape or operation).

The position confirming operations of the pipettes P of the reagent dispensing sections 90a to 90c are performed by inserting the pipettes P into the holes 211 of the position confirming members 210. When the pipette P is normal, the pipette P is rarely brought into contact with the position confirming member 210. Consequently, the pipette P and the position confirming member 210 can be prevented from being contaminated.

In addition, the position confirming operations of the pipettes P of the reagent dispensing sections 90a to 90c are immediately performed after the pipettes P are cleaned (Steps S4 to S6). Consequently, the position confirming member 210 can be prevented from being contaminated by the contact or approximation of the pipette P to the position confirming member 210.

The position confirming operations of the pipettes P of the reagent dispensing sections 90a to 90c are performed before the sample is dispensed by the sample dispensing section 50. Consequently, even if it is found that the pipette P has a problem and the measurement is stopped, the sample is not wasted.

The invention is not limited to the above-mentioned embodiments and its design can be properly changed.

For example, in the above-mentioned embodiments, the collision detecting sensor 170 is used as the position confirming sensor of the pipette P. However, a sensor made for position confirmation may be separately provided. For example, a transmission type sensor having a light projecting section and a light receiving section is used as the position confirming member 210 to detect whether the tip end of the pipette P has been inserted between the light projecting section and the light receiving section (space) by the transmission type sensor.

Moreover, in the above-mentioned embodiments, the measurement control section 140 is configured so as to confirm the position of the tip end of the pipette P. However, the position confirmation of the pipette can be performed by confirming a position of a middle part of the pipette P or a position of the liquid ejected from the pipette.

The position confirming operations of the pipettes P of the reagent dispensing sections 90a to 90c may be performed at predetermined intervals (for example, at intervals of 30 minutes) when the immunological analyzer 1 is in a standby state. In this case, even if the user touches the pipette P during the standby state and the pipette P is thereby bent, it can be detected that the pipette P is bent before the measurement is started. Consequently, it is possible to prevent that reliability of the measurement result is lowered by insufficient cleaning of the pipette P or a damage of the pipette P through the collision with the reagent container or the like, resulting from the start of the measurement with the bent pipette P.

The immunological analyzer 1 according to the above-mentioned embodiments has the position confirming member 210 made for position confirmation in order to perform the position confirming operation of the pipette P. However, the reagent containers 201 are 202 or the cleaning container 221 can be used as the position confirming member. In this case, the openings of the reagent containers 201 and 202 or the opening of the cleaning container 221 are formed as a hole (space) and determining whether the pipette P has been inserted into the hole is performed. Therefore, the position of the tip end of the pipette P can be confirmed. However, as described above, when the position confirming member 210 made for position confirmation is used, the diameter of the hole 211 can be freely decided and thus the position confirming operation of the pipette P can be more accurately performed.

The immunological analyzer 1 according to the above-mentioned embodiments is configured so as to perform the position confirming operations of the pipettes P of the reagent dispensing sections 90a to 90c, but may be configured so as to perform the position confirming operation of the pipette of the sample dispensing section 50.

The invention is not limited to the immunological analyzer and can be applied to other analyzers such as a blood-clotting measuring device, a multiple blood cell analyzer, an in-urine physical component analyzer and a genetic amplification measuring device.

What is claimed is:

1. A sample analyzer comprising:
a measurement unit including
a sample transporting section for transporting a rack on which a plurality of test tubes are placed,
a sample dispensing section for dispensing a sample in a test tube placed on the rack into a cuvette,
a plurality of reagent dispensing sections, each of the reagent dispensing sections including a pipette and a collision detecting sensor for detecting collision of the pipette, for aspirating a plurality of reagents in reagent containers and dispensing the aspirated reagents into the cuvette with the pipettes,
a detecting section for measuring the sample in the cuvette,
a plurality of position confirming members, which are different from the reagent containers and the cuvette, each of the position confirming members defining a space into which a tip end of the pipette of a reagent dispensing section can be inserted, and
a controller programmed for performing operations including
(i) receiving a measurement start signal in a standby state of the sample analyzer in which the sample analyzer is ready to start measurement,
(ii) controlling the plurality of reagent dispensing sections to insert the pipette of at least one of the reagent dispensing sections into the space defined by a position confirming member in response to the measurement start signal,
(iii) if, for each of the reagent dispensing sections, the collision detecting sensor did not detect collision of the pipette with the position confirming member in the controlling operation (ii), initiating sequential measurements of samples, and
(iv) if, for any of the reagent dispensing sections, the collision detecting sensor detected collision of the pipette with the position confirming member in the controlling operation (ii), stopping overall operation of the measurement unit, including reagent dispensing operations in each of the reagent dispensing sections and sample measurement operations in the detecting section, and sending an error signal; and
a control device in communication with the measurement unit, the control device including
a display section; and
a controller programmed for performing operations including
(i) displaying on the display section a standby option in response to receiving the error signal from the measurement unit, and
(iii) returning the sample analyzer to the standby state in response to receiving a user selection of the standby option, wherein measurement of a sample includes transporting a test tube containing the sample to a position corresponding to the sample dispensing section, dispensing the sample into a cuvette by the sample dispensing section, dispensing reagents into the cuvette by the reagent dispensing sections and measuring the sample in the cuvette by the detecting section.

2. The sample analyzer of claim 1, wherein each of the reagent dispensing sections includes an arm section movably supporting the pipette of the reagent dispensing section, and the collision detecting sensor of the reagent dispensing section is configured to detect the collision of the pipette by sensing a movement of the pipette with a position confirming member relative to the arm section.

3. The sample analyzer of claim 2, wherein each of the reagent dispensing sections further comprises:
an urging member coupled with the pipette of the reagent dispensing section for urging the pipette downwardly;
a base member movably mounted in the arm section of the reagent dispensing section so as to be movable together with the pipette relative to the arm section; and
a sensing member attached to the base member so as to normally shield transmission of light between a light projection section and a light receiving section of the light transmission sensor,
wherein the collision detecting sensor of the reagent dispensing section includes a light transmission sensor secured to the arm section for sensing that the sensing member moves relative to the arm section.

4. The sample analyzer of claim 1, further comprising a plurality of pipette cleaning sections, each of the plurality of pipette cleaning sections including a cleaning container having a cleaning hole for receiving the pipette of a reagent dispensing section and a cleaning nozzle for ejecting a cleaning liquid into the cleaning hole.

5. The sample analyzer of claim 4,
wherein the controller is further programmed to control the plurality of reagent dispensing sections to insert the pipette of each of the reagent dispensing sections into a cleaning hole of a pipette cleaning section and control the pipette cleaning section to initiate an ejecting of the cleaning liquid by the cleaning nozzle to clean the pipette in response to the measurement start instruction before the controlling operation (ii).

6. The sample analyzer of claim 1, wherein the controller is programmed to perform an initializing process after the sample analyzer is turned ON, and is programmed to set the sample analyzer in the standby state after the initializing process is completed, wherein the initializing process includes returning the pipette of each of the reagent dispensing sections to an origin position from which the controlling operation (ii) is performed.

7. The sample analyzer of claim 1, wherein the controller is further programmed for displaying on the display section pipette error information in response to receiving the error signal from the measurement unit.

8. The sample analyzer of claim 1,
wherein the controller is further programmed to control the plurality of reagent dispensing sections to insert the pipette of each of the reagent dispensing sections into the space defined by a position confirming member at predetermined intervals when the sample analyzer is kept on the standby state.

9. A method for measuring a sample in a sample analyzer that includes a measurement unit in communication with a control device, the method comprising:

(i) receiving, via the measurement unit, a measurement start signal in a standby state of the sample analyzer;
(ii) inserting, via the measurement unit, at least one of a plurality of pipettes into a space defined by one of a plurality of position confirming members in response to the measurement start signal;
(iii) if, for each of the pipettes, a collision of the pipette with the position confirming member was not detected in the inserting operation (ii), initiating, via the measurement unit, sequential measurements of samples, wherein measurement of a sample includes transporting a test tube containing the sample to a position corresponding to a sample dispensing section of the measurement unit, dispensing the sample from the test tube into a cuvette by the sample dispensing section, dispensing reagents into the cuvette by the pipettes and measuring the sample in the cuvette by a detecting section of the measurement unit;
(iv) if, for any of the pipettes, a collision of the pipette with the position confirming member was detected in the inserting operation (ii), stopping, via the measurement unit, overall operation of the measurement unit, including reagent dispensing by the pipettes and sample measuring by the detecting section, and sending an error signal to the control device;
(v) displaying, via the control device, on a display section of the control device pipette error information and a standby option in response to receiving the error signal from the measurement unit; and
(vi) returning, via the control device, the sample analyzer to the standby state in response to receiving a user selection of the standby option.

10. The method of claim 9 further comprising displaying, via the control device, on the display section of the control device pipette error information in response to receiving the error signal from the measurement unit.

11. A computer program product for using a sample analyzer that includes a measurement unit in communication with a control device, the computer program product comprising:
at least one computer readable medium; and
instructions, on the at least one computer readable medium, executable by at least one programmed processor to perform operations comprising:
(i) receiving a measurement start signal instruction in a standby state of the sample analyzer;
(ii) controlling a plurality of reagent dispensing sections of the measurement unit to insert a pipette of at least one of the reagent dispensing sections into a space defined by a position confirming member in response to the measurement start signal;
(iii) if, for each of the reagent dispensing sections, the collision detecting sensor did not detect collision of the pipette with the position confirming member in the controlling operation (ii), initiating sequential measurements of samples by the measurement unit, wherein measurement of a sample includes transporting a test tube containing the sample to a position corresponding to a sample dispensing section of the measurement unit, dispensing the sample from the test tube into a cuvette by the sample dispensing section, dispensing reagents into the cuvette by the pipettes of the reagent dispensing sections and measuring the sample in the cuvette by a detecting section of the measurement unit;
(iv) if, for any of the reagent dispensing sections, the collision detecting sensor detected collision of the pipette with the position confirming member in the controlling operation (ii), stopping overall operation of the measurement unit, including reagent dispensing by the pipettes and sample measuring by the detecting section, and sending an error signal to the control device;

(v) displaying on a display section of the control device a standby option in response to receiving the error signal from the measurement unit; and (vi) returning the sample analyzer to the standby state in response to receiving a user selection of the standby option.

12. The computer program product of claim 11, wherein the operations further comprise displaying on the display section of the control device pipette error information in response to receiving the error signal from the measurement unit.

\* \* \* \* \*